(12) United States Patent
Giuffrida et al.

(10) Patent No.: US 11,363,982 B1
(45) Date of Patent: Jun. 21, 2022

(54) METHOD AND SYSTEM FOR QUANTIFYING MOVEMENT DISORDER SYMPTOMS

(71) Applicant: Great Lakes NeuroTechnologies Inc., Cleveland, OH (US)

(72) Inventors: Joseph P. Giuffrida, Hinckley, OH (US); Dustin A. Heldman, Shaker Heights, OH (US)

(73) Assignee: Great Lakes NeuroTechnologies Inc., Cleveland, OH (US)

(*) Notice: Subject to any disclaimer, the term of this patent is extended or adjusted under 35 U.S.C. 154(b) by 382 days.

(21) Appl. No.: 16/541,347

(22) Filed: Aug. 15, 2019

Related U.S. Application Data

(63) Continuation of application No. 12/250,792, filed on Oct. 14, 2008, now abandoned.

(51) Int. Cl.
*A61B 5/00* (2006.01)
*A61B 5/11* (2006.01)
(Continued)

(52) U.S. Cl.
CPC .......... *A61B 5/4082* (2013.01); *A61B 5/0022* (2013.01); *A61B 5/1101* (2013.01); *A61B 5/6824* (2013.01); *A61B 5/6826* (2013.01); *A61B 5/7264* (2013.01); *A61B 5/7282* (2013.01); *A61K 31/198* (2013.01); *A61M 5/1723* (2013.01); *A61N 1/36067* (2013.01);
(Continued)

(58) Field of Classification Search
CPC .................................................. A61B 5/4082
See application file for complete search history.

(56) References Cited

U.S. PATENT DOCUMENTS

| 2005/0234309 A1* | 10/2005 | Klapper | A61B 5/7264 600/300 |
| 2005/0240086 A1* | 10/2005 | Akay | A61B 5/6825 600/300 |

(Continued)

FOREIGN PATENT DOCUMENTS

| WO | WO-2006088415 A1 * | 8/2006 | ............ A61B 5/1124 |
| WO | WO-2007062519 A1 * | 6/2007 | ............. A61B 5/112 |

*Primary Examiner* — Robert A Sorey
(74) *Attorney, Agent, or Firm* — Brian Kolkowski

(57) ABSTRACT

A system and method for scoring movement disorder symptoms comprises a movement measurement data acquisition system and processing comprising kinematic feature extraction and an algorithm trained using Unified Parkinson's Disease Rating Scale (UPDRS) scores from skilled clinicians. The movement data acquisition system, or "movement measuring apparatus," may comprise sensors such as accelerometers or gyroscopes or may utilize motion capture and/or machine vision technology or various other methods to measure tremor, bradykinesia, dyskinesia, or other movement disorders in a subject afflicted with Parkinson's disease, essential tremor or the like. The method outputs, and system displays, a score that uses the same scale as the UPDRS but has greater resolution and lower variability. In some embodiments, the system is used to diagnose and/or treat the patient by providing recommendations for treatment and/or by supplying treatment in the form of pharmaceutical drugs and/or electric stimulus as part of a closed-loop system.

20 Claims, 2 Drawing Sheets

(51) Int. Cl.
  *A61K 31/198*   (2006.01)
  *A61N 1/36*    (2006.01)
  *G16H 40/63*   (2018.01)
  *A61M 5/172*   (2006.01)

(52) U.S. Cl.
  CPC ......... *A61N 1/36139* (2013.01); *G16H 40/63* (2018.01); *A61B 2562/0219* (2013.01); *A61M 2230/63* (2013.01)

(56) References Cited

U.S. PATENT DOCUMENTS

| | | | |
|---|---|---|---|
| 2009/0118786 A1* | 5/2009 | Meadows | A61N 1/36185 607/45 |
| 2009/0192556 A1* | 7/2009 | Wu | A61B 5/291 607/3 |
| 2010/0030119 A1* | 2/2010 | McNames | A61B 5/4082 600/595 |
| 2010/0169409 A1* | 7/2010 | Fallon | G16H 10/60 707/802 |

* cited by examiner

US 11,363,982 B1

METHOD AND SYSTEM FOR QUANTIFYING MOVEMENT DISORDER SYMPTOMS

CROSS-REFERENCE TO RELATED APPLICATIONS

This application is a continuation of U.S. patent application Ser. No. 12/250,792, which was filed on Oct. 14, 2008.

LICENSE RIGHTS-FEDERAL SPONSORED

The U.S. Government has a paid-up license in this invention and the right in limited circumstances to require the patent owner to license others on reasonable terms provided for by the terms of the Phase II grant number 5R44NS043816-03 awarded by the National Institutes of Health, National Institute of Neurological Disorders and Stroke and grant number 1R44NS063454-01 awarded by the National Institutes of Health, National Institute on Aging.

TECHNICAL FIELD

The present invention relates to diagnostic medical apparatus, systems, devices and/or methods, and more particularly, to apparatus and methods for quantifying the severity of movement disorders, such as those associated with Parkinson's disease, including tremor, bradykinesia, and dyskinesia.

BACKGROUND

The current standard in evaluating the severity of movement disorder symptoms is the Unified Parkinson's Disease Rating Scale (UPDRS). Patients are typically scored by a certified trained clinician during an office visit. The UPDRS includes a number of tests used to score movement disorders, many of which involve repetitive movement tasks such as touching the nose and drawing the hand away repeatedly, or rapidly tapping the fingers together. Each test is evaluated by a clinician based solely on visual observation and graded on a scale that ranges from 0 (normal) to 4 (severe disorder). Even though numerical values are assigned, UPDRS scores are qualitative assessments and have been shown to vary considerably both between different evaluators of the same test and between the same evaluator's assessment of the same test scored at different times. The subjective assignment of UPDRS scores may mean that two experienced clinicians may assign greatly differing score values to a patient's performance of a test, even if the two clinicians base their scores on the same videorecorded performance. Even more troubling, the same clinician may assign greatly differing scores when making an assessment from the same videorecorded test viewed at different times. Additionally, while the UPDRS standard calls only for the assignment of discrete-integer score values (0, 1, 2, 3, or 4, for normal, slight, mild, moderate, and severe), some clinicians assign scores further specified by decimal fractions (2.3 or 3.5, e.g.), complicating diagnosis by assigning score values for which there is no universally agreed-upon significance.

Moreover, insightful gauging of movement disorder symptoms from the interpretation of a single examination, particularly in patients with motor fluctuations, is not as efficacious as would be periodic, objective monitoring of symptoms, particularly if such monitoring could be conducted at home.

Because prescribed treatments, including dosages of dopaminergic pharmacological drugs such as levodopa, many times are based in part on these scores, the evaluation of the efficacy of treatment protocols and the improvement of overall patient management is dependent upon the meaningfulness and reliability of scores assigned to assess movement disorder symptoms and thus upon the objectivity, accuracy, resolution, and frequency of the measurements upon which the scores are based.

One currently-marketed system for quantifying Parkinson's disease symptoms, that of Motus Bioengineering Inc., uses a miniature gyroscope to measure rotational motion on a hand and a data acquisition system to send measured rotational motion data to a processor. The processor then computes several simple statistics such as displacement and peak frequency. Another currently-marketed system, that of FlexAble Systems, Inc., uses a miniature 3-axis accelerometer to measure linear acceleration on a hand and a data acquisition system to send measured linear acceleration data to a processor. The processor then likewise computes several simple statistics such as weighted mean frequency of tremor, frequency spread, tremor amplitude and percent tremor time, and further computes a simple score by multiplying these statistics together. However, neither system is capable of providing a score that approximates or is predictive of a score given on the Unified Parkinson's Disease Rating Scale, and further, neither system is capable of providing a score that is based in part on reference data or uses an algorithm that has been trained from reference data consisting of UPDRS scores given by clinicians.

U.S. patent application Ser. No. 11/030,490 of Klapper, filed Jan. 5, 2005, herein incorporated by reference, describes a system of five accelerometers placed in different positions over the entirety of the body of a Parkinson's patient to acquire movement measurements and thereby stage, or classify movement states of, patients exhibiting bradykinesia and dyskinesia by continuously collecting data over extended time spans (hours or days). A test that can be administered rapidly, for example, in just a few minutes, would be preferable to the one described in the application of Klapper, as it could be performed either at home or in a brief visit to a doctor's office. Further, use of a small number of judiciously-placed sensors, or a system capable of detecting body movements without the placement of sensors on the body, would be less cumbersome for a subject than is placing sensors in a large number of locations, and would therefore have the advantage of being more readily acceptable. A test capable of quantifying the symptoms of bradykinesia, dyskinesia, and tremor is also more desirable than a test capable of evaluating only a subset of these common movement disorders. The quantification algorithm described in the application of Klapper describes prediction of a patient's self-assessment scores, but the capability to generate scores that correlate to UPDRS scores of trained clinicians would be the more valuable determination.

Two publications of Arash Salarian et al. ("An ambulatory system to quantify bradykinesia and tremor in Parkinson's disease," *Information Technology Applications in Biomedicine*, 2003, 4th International IEEE EMS Special Topic Conference on, 2003, pp. 35-38, and "Quantification of tremor and bradykinesia in Parkinson's disease using a novel ambulatory monitoring system," *IEEE Transactions on Biomed Engineering*, Vol. 54, No. 2, February 2007, pp. 313-22) describe a wrist-mounted, 2-gyroscope-based system for quantifying tremor and bradykinesia in Parkinson's disease patients, and report correlation with UPDRS scores. However, this UPDRS tremor correlation was computed by combining rest and postural scores, whereas computing correlations for the scores separately is essential to determining valid correlations with UPDRS scores given for the different tests on the UPDRS motor exam. As with the system described in Klapper, the system of Salarian examines data from continuous long-term recordings, and requires over 5 minutes of recorded data to produce significant correlations. A preferred system would record data for individual tests given in only 15-20 seconds. The worn apparatus of the system described by Salarian weighs 35 grams, or 50 grams with a data logger for wireless operation, whereas a preferred worn apparatus would weigh less than 15 grams, or, ideally, would weigh nothing at all on the body.

It is therefore the object of the present invention to provide a method and system for objectively quantifying Parkinson's disease manifestations by providing symptom scores that are readily comprehensible to clinicians as being in the same scale as, and substantially correlative to, scores given on the Unified Parkinson's Disease Rating Scale. This method should eliminate clinician subjectivity while providing quantitative scores of improved resolution. It is further the object of the present invention to provide such a method and system with improved time and frequency resolution that will aid in evaluating efficacy of treatment protocols and improve patient management. It is yet further the object of the present invention to provide such a method and system used to recommend a treatment or a treatment adjustment, or to directly control treatment in an automated closed-loop treatment system. Predicate to all the above, it is the object of the present invention to record movement data from subjects as they complete motor tasks, process that data into quantitative kinematic features that describe movement disorder symptom severity, and use those kinematic features as inputs to a trained algorithm to output tremor scores highly correlated to clinician UPDRS scores.

As the Unified Parkinson's Disease Rating Scale is broadly taught, accepted and practiced by clinicians, the movement disorder quantification system of the present invention advantageously produces scores that approximate or mirror reliable UPDRS scores, promoting ready acceptance of the invention as an improved standard for patient diagnosis, monitoring, and treatment.

SUMMARY

The present invention relates to methods for quantifying movement disorders for the diagnosis and treatment of patients who exhibit the symptoms of Parkinson's disease and the like. The present invention further relates to an algorithm trained using reference data, particularly where the data comprises clinician-assigned movement disorder test scores given on the Unified Parkinson's Disease Rating Scale, and more particularly when the scores are given for tests from the UPDRS motor examination.

Objective quantification of a subject's movement disorder symptoms, including tremor, bradykinesia and dyskinesia, requires as a first step measurement of the movement. This measurement can be performed by measuring a single parameter or different parameters; the parameter or parameters being measured may include linear or rotational displacement, velocity, or acceleration, electromyographic (EMG) signals, or any other parameter that could give a quantitative indication of motion; and the part of the body being measured for motion may be a limb (as at a wrist, ankle, or finger) or may be the trunk of the body (as at a shoulder or torso) and by other techniques known to those skilled in the art. Sensors used for measuring body motion include gyroscopes and accelerometers, preferably miniaturized; electromagnets; EMG; video; or other sensors known to those skilled in the art. Other systems that can be used to detect and measure body motion include motion capture systems, machine vision systems, sonic or laser Doppler velocity transducers, infrared systems, GPS, or any other system known to those skilled in the art. The movement data acquisition system, or "movement measuring apparatus," used in the present invention may incorporate one or more of any of the above sensors or systems. A pre-existing movement data acquisition system, such as the one described in patent application Ser. No. 11/082,668, herein incorporated by reference, may similarly be used. In the present disclosure, "movement data" is construed as including, but not being limited to, any signal or set of signals, analog or digital, corresponding to movement of any part of the body or multiple parts of the body, independently or in conjunction with each other. Movement may be continuously measured over long time spans, or may be measured only over a short time span, for example, during the period of only one or several tests taken from or modified from the UPDRS motor exam. In certain embodiments of the present invention, the measurement time needed to produce a score substantially predictive of a UPDRS score for a given test on the UPDRS motor exam is acquired during a test lasting no more than about 20 seconds. Further, in certain embodiments of the present invention, the measurement time needed to produce scores substantially predictive of a set of multiple UPDRS scores for multiple given tests on the UPDRS motor exam is acquired during a test preferably lasting no more than about 30 minutes. More preferably, the measurement time does not exceed 15 minutes. More preferably, the measurement time does not exceed 10 minutes. Even more preferably, the measurement time does not exceed 5 minutes. Even still more preferably, the measurement time does not exceed 3 minutes.

Following measurement of symptomatic movement, the next step in objective quantification of a subject's movement disorder symptoms is the extraction of statistical kinematic features from the acquired movement data via processing. This processing may take place during or following data acquisition and may occur within a movement data acquisition device or within a different processing device, such as a personal computer, PDA, smart phone, or the like, with which the acquisition device interfaces, either through a cable connection or by wireless transmission. Useful kinematic features that may be extracted from gyroscopic data may include, for example, peak power angular velocity, peak power angle, RMS angular velocity, frequency, maximum amplitude, maximum peak-to-peak amplitude, mean angular velocity, and wavelet parameters, as well as the covariance or standard deviation over time of any of these parameters. Useful kinematic features that may be extracted from accelerometer data may include, for example, peak power acceleration, peak power velocity, peak power position, RMS acceleration, RMS velocity, RMS position, frequency, maximum amplitude, maximum peak-to-peak amplitude, mean acceleration, and wavelet parameters, as well as the covariance or standard deviation over time of any of these parameters. In a movement data acquisition system, or movement measuring apparatus, that combines a three-axis accelerometer and a three-axis gyroscope to produce 6 channels of movement data, one or any combination of the above kinematic features can be extracted from any of the 6 kinematic channels to be used as inputs to a trained algorithm in the next step. The listed kinematic features for the sensors above are intended to be exemplary, and not limiting; other types of sensors will produce different data from which different sets of features may be extracted.

The trained algorithm used to process the kinematic features extracted from the movement data may comprise, for example, one or more of a simple or multiple linear regression, an artificial neural network, a Bayesian network, or a genetic algorithm. The output of the trained algorithm may be a single score or multiple scores of any scale; a single score on the same scale as that of the UPDRS may be preferred in certain applications where simplicity or familiarity is the paramount concern, while more sophisticated scores and scales may be preferred for other advanced applications, such as those that involve recommendations for treatment or closed-loop automated treatment delivery.

A number of embodiments of the present invention are envisioned in this disclosure.

In one embodiment, the system for quantifying movement disorder symptoms of the present invention comprises a movement measuring apparatus to acquire data corresponding to movement of the body of a subject, a processor capable of processing the acquired movement data with an algorithm for calculating a score based at least in part on the movement data, where the algorithm is based at least in part on reference data, and, optionally, a display showing the score. The reference data may comprise UPDRS scores given by preferably at least two trained clinicians, and the score may be limited to real number values between 0 and 4, inclusive.

In another embodiment, the present invention constitutes a method for quantifying symptoms of a movement disorder of a subject, comprising measuring the movement of a subject's limb to acquire movement data, processing the movement data to extract at least one kinematic feature, and processing the at least one kinematic feature using a trained algorithm to determine a score, where the algorithm is trained using reference data that includes UPDRS scores given by at least two clinicians, and where the score is used for the diagnosis or treatment of the subject.

In yet another embodiment, the system for quantifying movement disorder symptoms of the present invention comprises a movement measuring apparatus to acquire data corresponding to movement of the subject, a processor capable of processing the acquired movement data with an algorithm for calculating a score based at least in part on the movement data, where the algorithm is based at least in part on reference data that includes UPDRS scores given by at least two clinicians, and an output of a signal corresponding to a recommendation for treatment, where said recommendation is derived at least in part from the processed movement data.

Preferably, the movement measuring apparatus is small, lightweight, and not cumbersome. In some embodiments of the present invention, the movement measuring apparatus preferably consists only of one or two sensor packages placed only on the wrist and finger of the subject and weighs no more than about 3.4 ounces. More preferably, the movement measuring apparatus consists of a sensor package placed only on the finger of the subject and weighs no more than half an ounce. Even more preferably, in other embodiments, the movement measuring apparatus is machine vision-based and uses a video camera or similar sensor to detect the motion of the subject without any sensor devices placed on the body of the subject.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention and together with the description serve to explain the principles and operation of the invention.

DESCRIPTION OF THE PREFERRED EMBODIMENTS

Figure 1A:
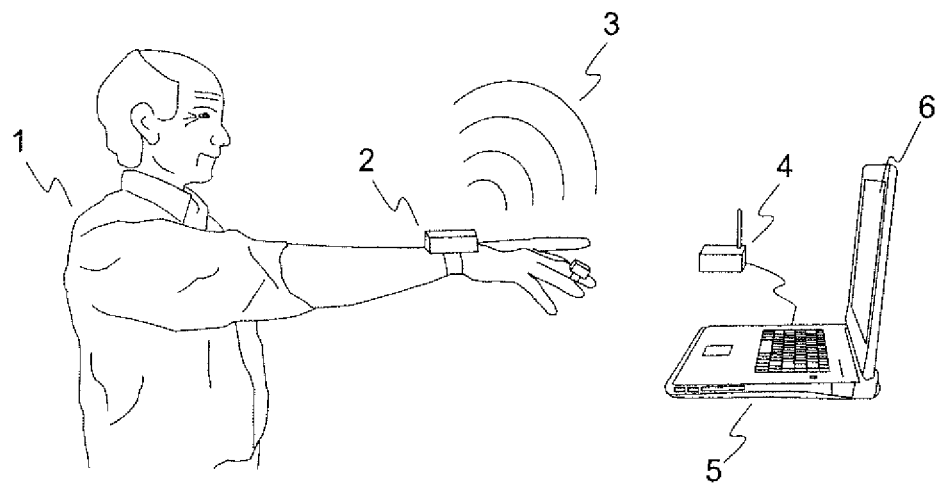
FIGS. 1A-B. Schematic views of subject kinematics being measured with movement measuring apparatus in two different embodiments of the present invention.

The present invention relates to the quantification of movement disorders in a movement disorder monitor, and a method of objectively quantifying the severity of a subject's movement disorder. Preferably, this quantification is reduced to a simple score on a scale equivalent to that of the UPDRS. The present invention additionally relates to the use of such quantification to provide recommendation for treatment or as part of a treatment delivery system for automatically dosing a subject with a pharmaceutical drug or for supplying some part of the nervous system of the subject with an electrical stimulus in response to the quantified level of severity of a subject's symptoms.

The systems and methods of the various embodiments of the present invention are used to analyze, score, and treat various movement disorders. Movement disorders for purposes of this application include but are not limited to Parkinson's disease and essential tremor. Some of the treatments used for these disorders involve pharmaceutical interventions, fetal cell transplants, surgery, or deep brain stimulation. The efficacy of these interventions is often judged by the interventions ability to alleviate subject symptoms and improve subject quality of life. The subject on which system or method is used is a human or another form of animal.

The present invention includes a trained algorithm to determine scoring from movement data acquired by a movement measuring apparatus. The trained algorithm in part comprises a mathematical model or quantitative representation, used to process kinematic features computed from the movement data and may include some of those steps known to those skilled in the art. In the development of one of the algorithms of the present invention, a movement data acquisition system comprising a three-axis accelerometer and a three-axis gyroscope was used to collect data from 60 Parkinson's disease subjects as they completed a subset of the UPDRS upper extremity motor exam including rest, postural, and kinetic tremor. For some patients, each arm was tested once when symptoms were occurring. In others, the more affected arm was tested twice, once with and once without symptoms. For this group, symptoms were controlled by timing of medication or turning on and off deep brain stimulation. In all, 87 total trials were performed with a variety of patient tremor symptoms.

Subjects were videotaped and rated on the UPDRS (0-4) by two movement disorder neurologists. Their two scores were averaged.

The six kinematic signals were band pass filtered to 3-10 Hz using a second-order Butterworth filter. The power spectrum of each signal was calculated using an FFT. Several time- and frequency-based measures were computed for each channel of movement data including the peak power, frequency of the peak power, root mean square (RMS) of the angular velocity, and RMS of the angle.

A multiple linear regression model was used to correlate quantitative kinematic features of the kinematic signals with the average clinician UPDRS score for each tremor task. The following linear model was used to regress the average clinician scores against the computed quantitative variables:

$$R = b_0 + \vec{B}_a \cdot \vec{P}_a + \vec{B}_g \cdot \vec{P}_g \qquad (1)$$

where R is the clinician's score and $\vec{B}_a$, $\vec{B}_g$, $\vec{P}_a$, and $\vec{P}_g$ are all 3-dimensional vectors. $\vec{P}_a$ and $\vec{P}_g$ are the quantitative variables for the three accelerometers and three gyroscopes, respectively, $\vec{B}_a$, $\vec{B}_g$, and $b_0$ are the regression coefficients, and • is the dot product operator. This model can be rewritten as:

$$R = b_0 + B_{ax} P_{ax} + B_{ay} P_{ay} + B_{az} P_{az} + B_{gx} P_{gx} + B_{gy} P_{gy} + B_{gz} P_{gz} \qquad (2)$$

Out of all the kinematic features examined, logarithm of the peak power for all six channels correlated best for rest and postural tremor, while the RMS amplitude of all six channels correlated best for kinetic tremor.

The values of $\vec{B}_a$, $\vec{B}_g$, and $b_0$ that were determined from the regression (EQ. 1) for each task can now be used in the algorithm to generate scores: data can recorded by the movement measuring apparatus and processed to extract kinematic features $\vec{P}_a$ and $\vec{P}_g$, which values are then input back into EQ. 1 to get R, the generated score. (Scores below 0 or above 4 are rounded to 0 or 4, respectively.)

Figure 1B:
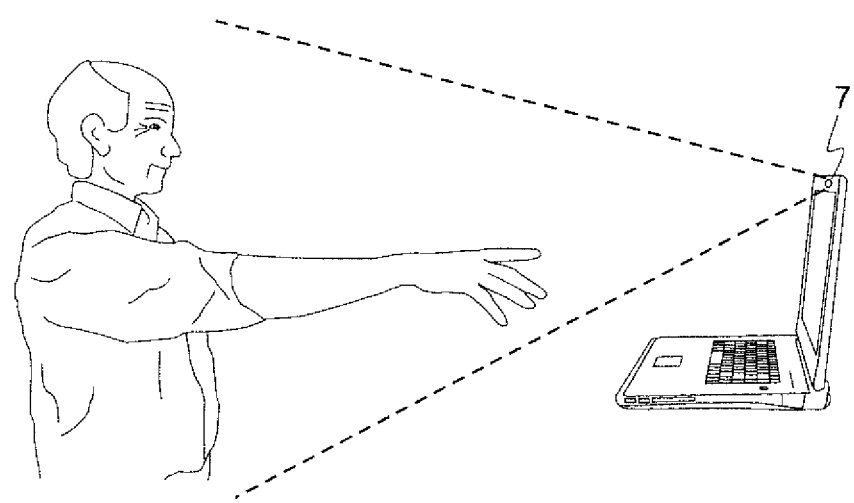

FIGS. 1A-B shows the data collection process for two different embodiments of the present invention. In FIG. 1A), a subject 1 wears a sensor unit 2 comprising accelerometers and gyroscopes (both not shown) as well as a transmission system (not shown). The transmission system may be wired or wireless, and may communicate via any medium and any transmission protocol known to someone skilled in the art. In the illustrated embodiment, the subject 1 performs a movement disorder test according to instructions and, optionally, an instructional video displayed on a monitor 6 and/or according to instructions given by a clinician. The sensor unit 2 transmits the subject's movement data via radio link 3 to a receiver unit 4, which is plugged into a computer 5 via USB. The processor of the computer 5 processes the movement data to extract kinematic features which are then fed into a trained algorithm implemented as a software algorithm in the computer 5. The trained algorithm outputs a score which may then be displayed on the monitor 6. The processor may also create an output to a treatment device (not shown), which output is used to control such device. FIG. 1B) illustrates substantially the same process with a different form of movement measuring apparatus. In FIG. 1B), a camera 7, which may be a webcam built into a computer (as illustrated) or may be a separate camera or set of multiple cameras (not shown) connected to a computer, which view the subject performing the motion disorder test and feeds video data into the computer where, for example, machine vision algorithms measure the motion of the limbs of the subject with respect to time according to any method known in the art. Such a method may consist, for example, in determining marker points along the limb of the subject in order to gauge relative motion, and such a method may be assisted by applying more visible markers (not shown) on various points on the limb of a subject, such as is common with motion capture technology. Thus in FIG. 1B) the need for sensor unit 2 of FIG. 1A), with its accelerometers and gyroscopes, is obviated.

Figure 2:
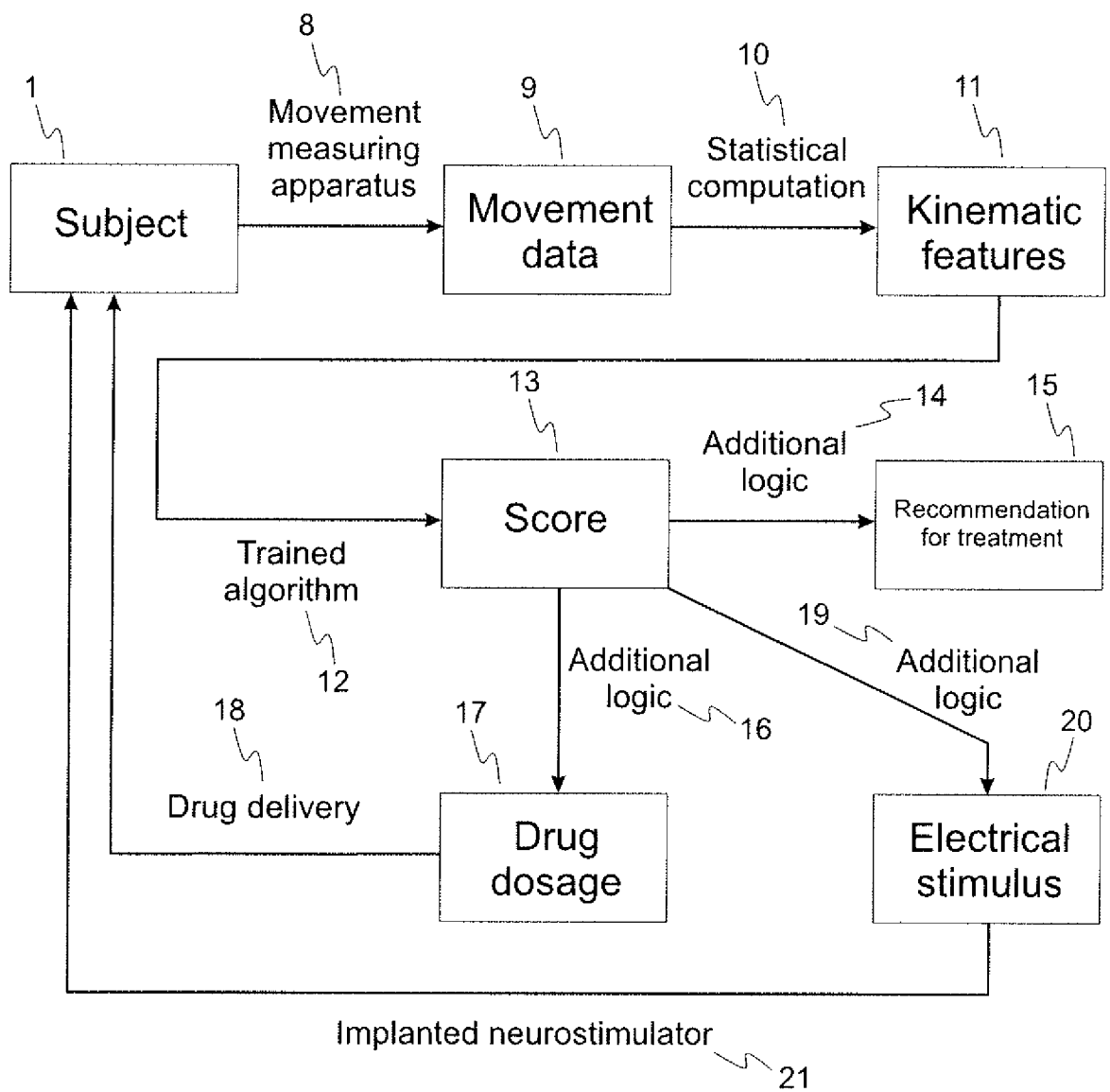
FIG. 2. Flow diagram of the quantification system in one embodiment of the present invention.

FIG. 2 shows one process of score calculation as a flow diagram. The movement measuring apparatus 8 may be of any type described above or any other type known to those skilled in the art. Movement data 9 are acquired from the subject 1 by the movement measuring apparatus 8. Kinematic features 11, extracted from the movement data 9 through statistical computation 10 inside a processor, are fed into a trained algorithm 12, which may be of any type described in this disclosure or of another type known to those skilled in the art, to determine the score 13. Where a score on the Unified Parkinson's Disease Ratings Scale is desired, this score is a real number between 0 and 4, inclusive. Certain additional logic 14 may generate from the score 13 a recommendation for treatment 15, while other additional logic 16 may determine a drug dosage 17 administered to the patient 1 through a drug delivery system 18 (e.g., an implantable pump), and still other additional logic 19 may determine the parameters for an electrical stimulus 20 administered to the patient 1 via an implanted neurostimulator 21 (a deep brain stimulation electrode probe, e.g.).

The movement disorder quantification system of the present invention can be tested for accuracy. According to one test method, movement data is collected from subjects with Parkinson's disease using the system while performing the standard upper extremity UPDRS motor exam, and the test is simultaneously scored, or videorecorded for subsequent scoring, by one or more skilled clinicians. Scores from multiple clinicians for the same subject's test may be combined or aggregated by averaging, weighted averaging, or any other known method. A linear regression may then be performed with the system scores as the predictor variable values and the clinician scores as the response variable values. The coefficient of determination ($R^2$) computed from the linear regression and the root-mean-square (RMS) error between the system scores and the averaged clinician scores then serve as measures of system reliability.

The reliability test itself becomes more reliable when the number of motor exam test scores collected is large, and when the number of clinician scores for each test is large. Preferably, scores from at least 60 motor exam tests are collected. More preferably, scores from at least 100 motor exam tests are collected. Still more preferably, scores from at least 200 motor exam tests are collected. Because of the variability between scores given by different skilled clinicians, it is important that the reference data used to train the system and method of the present invention does not rely on the scoring of only one clinician. Therefore, these motor exam tests are each scored by at least 2 skilled clinicians. Preferably, these tests are each scored by at least 5 skilled clinicians. More preferably, these tests are each scored by at least 7 skilled clinicians. For the purposes of this disclosure, the terms "skilled clinician" and "trained clinician," used interchangeably, refer to those clinicians who have received accreditation in UPDRS scoring from the Movement Disorders Society (as described in Goetz and Stebbins, "Assuring interrater reliability for the UPDRS motor section:

Utility of the UPDRS Teaching Tape", *Movement Disorders*, Vol. 19, No. 12, 2004, herein incorporated by reference), or the recognized equivalent.

Preferably, the coefficient of determination between the system scores and the averaged clinician scores for the rest tremor portion of the motor exam is greater than about 0.6. More preferably, the coefficient of determination between the system scores and the average clinician score for the rest tremor portion of the motor exam is greater than about 0.7. Even more preferably, the coefficient of determination between the system scores and the average clinician score for the rest tremor portion of the motor exam is greater than about 0.8. More preferably still, the coefficient of determination between the system scores and the average clinician score for the rest tremor portion of the motor exam is greater than about 0.85. Even more preferably, the coefficient of determination between the system scores and the average clinician score for the rest tremor portion of the motor exam is greater than about 0.9. Still more preferably, the coefficient of determination between the system scores and the average clinician score for the rest tremor portion of the motor exam is greater than about 0.95. Most preferably, the coefficient of determination between the system scores and the average clinician score for the rest tremor portion of the motor exam is greater than about 0.98.

Preferably, the coefficient of determination between the system scores and the averaged clinician scores for the postural tremor portion of the motor exam is greater than about 0.6. More preferably, the coefficient of determination between the system scores and the average clinician score for the postural tremor portion of the motor exam is greater than about 0.7. Even more preferably, the coefficient of determination between the system scores and the average clinician score for the postural tremor portion of the motor exam is greater than about 0.8. More preferably still, the coefficient of determination between the system scores and the average clinician score for the postural tremor portion of the motor exam is greater than about 0.88. Even more preferably, the coefficient of determination between the system scores and the average clinician score for the postural tremor portion of the motor exam is greater than about 0.9. Still more preferably, the coefficient of determination between the system scores and the average clinician score for the postural tremor portion of the motor exam is greater than about 0.95. Most preferably, the coefficient of determination between the system scores and the average clinician score for the postural tremor portion of the motor exam is greater than about 0.98.

Preferably, the coefficient of determination between the system scores and the averaged clinician scores for the kinetic tremor portion of the motor exam is greater than about 0.4. More preferably, the coefficient of determination between the system scores and the average clinician score for the kinetic tremor portion of the motor exam is greater than about 0.5. Even more preferably, the coefficient of determination between the system scores and the average clinician score for the kinetic tremor portion of the motor exam is greater than about 0.6. More preferably still, the coefficient of determination between the system scores and the average clinician score for the kinetic tremor portion of the motor exam is greater than about 0.7. Even more preferably, the coefficient of determination between the system scores and the average clinician score for the kinetic tremor portion of the motor exam is greater than about 0.8. Even more preferably, the coefficient of determination between the system scores and the average clinician score for the kinetic tremor portion of the motor exam is greater than about 0.9. Still more preferably, the coefficient of determination between the system scores and the average clinician score for the kinetic tremor portion of the motor exam is greater than about 0.95. Most preferably, the coefficient of determination between the system scores and the average clinician score for the kinetic tremor portion of the motor exam is greater than about 0.98.

Preferably, the RMS error between the system scores and the averaged clinician scores for the rest tremor portion of the motor exam is less than about 15%. More preferably, the RMS error between the system scores and the averaged clinician scores for the rest tremor portion of the motor exam is less than about 10%. Even more preferably, the RMS error between the system scores and the averaged clinician scores for the rest tremor portion of the motor exam is less than about 9%. More preferably still, the RMS error between the system scores and the averaged clinician scores for the rest tremor portion of the motor exam is less than about 8%. Even more preferably, the RMS error between the system scores and the averaged clinician scores for the rest tremor portion of the motor exam is less than about 5%.

Preferably, the RMS error between the system scores and the averaged clinician scores for the postural tremor portion of the motor exam is less than about 15%. More preferably, the RMS error between the system scores and the averaged clinician scores for the postural tremor portion of the motor exam is less than about 10%. Even more preferably, the RMS error between the system scores and the averaged clinician scores for the postural tremor portion of the motor exam is less than about 9%. More preferably still, the RMS error between the system scores and the averaged clinician scores for the postural tremor portion of the motor exam is less than about 8%. Even more preferably, the RMS error between the system scores and the averaged clinician scores for the postural tremor portion of the motor exam is less than about 5%.

Preferably, the RMS error between the system scores and the averaged clinician scores for the kinetic tremor portion of the motor exam is less than about 20%. More preferably, the RMS error between the system scores and the averaged clinician scores for the kinetic tremor portion of the motor exam is less than about 15%. Even more preferably, the RMS error between the system scores and the averaged clinician scores for the kinetic tremor portion of the motor exam is less than about 11%. More preferably still, the RMS error between the system scores and the averaged clinician scores for the kinetic tremor portion of the motor exam is less than about 10%. Even more preferably, the RMS error between the system scores and the averaged clinician scores for the kinetic tremor portion of the motor exam is less than about 8%.

For tests designed to evaluate bradykinesia, such as finger taps, hand grasps, and rapid alternating hand movements, coefficient of determination values are preferably greater than about 0.5, even more preferably greater than about 0.6, even more preferably greater than about 0.7, even more preferably greater than about 0.8, and still more preferably greater than 0.9; and RMS errors are preferably less than about 15%, more preferably less than about 12%, even more preferably less than about 10%, even more preferably less than about 8%, and still more preferably less than about 6%.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed:

1. A system adapted for quantifying symptoms of a movement disorder of a subject having a body with limbs, comprising:
   a movement measuring apparatus comprising a sensor unit comprising four or fewer sensors, including at least one accelerometer and at least one gyroscope, for measuring body motion adapted to acquire movement data corresponding to movement of the body of the subject while the subject performs at least one specific or individual Unified Parkinson's Disease Rating Scale (UPDRS) motor exam test the movement measuring apparatus adapted to be worn or attached on an upper extremity of the subject;
   a processor adapted to process the acquired movement data from the sensor unit to extract at least two different kinematic features related to severity of at least one movement disorder symptom related to the at least one UPDRS motor exam test, the processor further adapted to calculate a score representative of severity of the at least one movement disorder symptom based at least in part on the at least two kinematic features, and at least one of the at least two kinematic features is directed to a measure other than magnitude of the sensor signal;
   a processor output comprising the calculated score and/or treatment recommendations based at least in part on the calculated score; and
   a treatment delivery device adapted to receive the processor output and to provide treatment to the subject based at least in part on the calculated score and/or treatment recommendations,
   wherein the calculated score representative of severity of at least one movement disorder symptom is based at least in part on reference data comprising UPDRS scores given for motor exam tests scored by at least five trained clinicians and is predictive of a score given by a skilled clinician for the specific or individual UPDRS motor exam test.

2. The system of claim 1, wherein the reference data further comprises correlation data between measured kinematic features and UPDRS scores given by trained clinicians comprised in the reference data, and the processor is adapted to calculate the score with at least one of the at least two kinematic features selected based on its correlation to the specific or individual UPDRS motor exam test.

3. The system of claim 2, wherein the movement measuring apparatus wirelessly transmits the acquired movement data to a smart phone comprising the processor for processing the acquired movement data with the algorithm and the smartphone displays the score and is further adapted for outputting the processor output to the treatment device.

4. The system of claim 2, wherein at least one of the at least two kinematic features is selected from the group consisting of peak power acceleration, peak power velocity, peak power position, RMS acceleration, RMS velocity, RMS position, peak power angular velocity, peak power angle, RMS angular velocity, frequency, maximum amplitude, maximum peak-to-peak amplitude, mean acceleration, mean angular velocity, wavelet parameters, covariance over time of any of these parameters, and standard deviation over time of any of these parameters.

5. The system of claim 2, wherein the treatment delivery device is a drug delivery system.

6. The system of claim 2, wherein the treatment delivery device is a deep brain stimulation device.

7. The system of claim 2, wherein a coefficient of determination calculated between the calculated score and an average of the clinician scores in the reference data or trained clinician scores separately observed and provided by trained clinicians for the specific or individual UPDRS motor exam test is greater than 0.6.

8. A method for diagnosing and treating a subject having a movement disorder comprising the steps of:
   instructing a subject to perform at least one individual or specific Unified Parkinson's Disease Rating Scale (UPDRS) motor exam test while wearing a movement measuring apparatus on an upper extremity, the movement measuring apparatus comprising a sensor unit comprising four or fewer sensors, including at least one accelerometer and at least one gyroscope, adapted for measuring body motion of the subject;
   measuring movement of at least one limb of the subject with the movement measuring apparatus to acquire movement data while the subject performs the individual or specific UPDRS test;
   processing, with a processor, the sensor acquired movement data to extract at least two kinematic features related to severity of at least one movement disorder symptom, and at least one of the at least two kinematic features is directed to a measure other than magnitude of the sensor signal;
   processing, with the processor or another processor, the at least two kinematic features to calculate a score representative of severity of the at least one movement disorder symptom for the individual or specific test based at least in part on the at least two kinematic features;
   outputting a processor output comprising the calculated score and/or treatment recommendations based at least in part on the calculated score,
   receiving, with a treatment delivery device, the processor output, and adjusting treatment parameters of the treatment delivery device based at least in part on the calculated score and/or treatment recommendations; and
   providing treatment to the subject with the treatment delivery device according to the adjusted treatment parameters,
   wherein the calculated score representative of severity of at least one movement disorder is based at least in part on reference data comprising UPDRS scores given for motor exam tests scored by at least five trained clinicians and is predictive of a score given by a skilled clinician using the UPDRS rating scale for the individual or specific test.

9. The method of claim 8, wherein the reference data further comprises correlation data between measured kinematic features and UPDRS scores given by trained clinicians comprised in the reference data, and the processor is adapted to calculate the score with at least one of the at least two kinematic features selected based on its correlation to the specific or individual UPDRS motor exam test.

10. The method of claim 9, wherein the movement measuring apparatus wirelessly transmits the acquired movement data to a smart phone comprising the processor for processing the acquired movement data with the algorithm and the smartphone displays the score and is further adapted for outputting the processor output to the treatment device.

11. The method of claim 9, wherein at least one of the at least two kinematic features is selected from the group consisting of peak power acceleration, peak power velocity, peak power position, RMS acceleration, RMS velocity, RMS position, peak power angular velocity, peak power angle, RMS angular velocity, frequency, maximum amplitude, maximum peak-to-peak amplitude, mean acceleration, mean angular velocity, wavelet parameters, covariance over time of any of these parameters, and standard deviation over time of any of these parameters.

12. The method of claim 9, wherein the treatment delivery device is a drug delivery system.

13. The method of claim 9, wherein the treatment delivery device is a deep brain stimulation device.

14. The method of claim 9, a coefficient of determination calculated between the calculated score and an average of the clinician scores in the reference data or trained clinician scores separately observed and provided by trained clinicians for the specific or individual UPDRS motor exam test is greater than 0.6.

15. A system for diagnosing and treating a subject having a movement disorder, comprising
a movement measuring apparatus comprising a sensor unit comprising four or fewer sensors, including at least one accelerometer and at least one gyroscope, for measuring body motion adapted to acquire movement data corresponding to movement of the body of the subject, the movement measuring apparatus adapted to be worn or attached on an upper extremity of the subject;
a processor adapted to process the acquired movement data to extract at least two different kinematic features related to severity of at least one movement disorder symptom, the processor further adapted to calculate a score representative of severity of the at least one movement disorder symptom based at least in part on the at least two kinematic features, and at least one of the at least two kinematic features is directed to a measure other than magnitude of the sensor signal;
a processor output comprising the calculated score and/or treatment recommendations based at least in part on the calculated score; and
a treatment delivery device adapted to receive the processor output and to provide treatment to the subject based at least in part on the calculated score and/or treatment recommendations,
wherein the calculated score representative of severity of at least one movement disorder symptom is based at least in part on reference data comprising UPDRS scores given for motor exam tests scored by at least five trained clinicians and is predictive of a score given by a skilled clinician for the specific or individual UPDRS motor exam test.

16. The system of claim 15, wherein the reference data further comprises correlation data between measured kinematic features and UPDRS scores given by trained clinicians comprised in the reference data, and the processor is adapted to calculate the score with at least one of the at least two kinematic features selected based on its correlation to the specific or individual UPDRS motor exam test.

17. The system of claim 16, wherein at least one of the at least two kinematic features is selected from the group consisting of peak power acceleration, peak power velocity, peak power position, RMS acceleration, RMS velocity, RMS position, peak power angular velocity, peak power angle, RMS angular velocity, frequency, maximum amplitude, maximum peak-to-peak amplitude, mean acceleration, mean angular velocity, wavelet parameters, covariance over time of any of these parameters, and standard deviation over time of any of these parameters.

18. The system of claim 16, wherein the treatment delivery device is a drug delivery system.

19. The system of claim 16, wherein the treatment delivery device is a deep brain stimulation device.

20. The system of claim 16, wherein the movement measuring apparatus wirelessly transmits the acquired movement data to a smart phone comprising the processor for processing the acquired movement data with the algorithm and the smartphone displays the score and is further adapted for outputting the processor output to the treatment device.

* * * * *